(12) United States Patent
Schmitt

(10) Patent No.: US 7,322,824 B2
(45) Date of Patent: Jan. 29, 2008

(54) DESIGN AND MANUFACTURE OF DENTAL IMPLANT RESTORATIONS

(76) Inventor: Stephen M. Schmitt, 7826 Louis Pasteur #104, San Antonio, TX (US) 78222

(*) Notice: Subject to any disclaimer, the term of this patent is extended or adjusted under 35 U.S.C. 154(b) by 257 days.

(21) Appl. No.: 11/207,095

(22) Filed: Aug. 17, 2005

(65) Prior Publication Data

US 2006/0040236 A1 Feb. 23, 2006

Related U.S. Application Data

(60) Provisional application No. 60/602,390, filed on Aug. 17, 2004.

(51) Int. Cl.
*A61C 5/00* (2006.01)
(52) U.S. Cl. .................................................. 433/215
(58) Field of Classification Search ................. 433/215
See application file for complete search history.

(56) References Cited

U.S. PATENT DOCUMENTS

| | | | |
|---|---|---|---|
| 4,766,704 A | 8/1988 | Brandestini et al. |
| 4,837,732 A | 6/1989 | Brandestini et al. |
| 5,527,182 A | 6/1996 | Willoughby |
| 5,652,709 A | 7/1997 | Andersson et al. |
| 5,690,843 A | 11/1997 | Schmitt et al. |
| 5,697,997 A | 12/1997 | Aronsson et al. |
| 5,733,126 A | 3/1998 | Andersson et al. |
| 5,741,215 A | 4/1998 | D'Urso |
| 5,768,134 A | 6/1998 | Swaelens et al. |
| 5,779,477 A | 7/1998 | Boss |
| 5,800,174 A | 9/1998 | Andersson |
| 5,816,810 A | 10/1998 | Antonson et al. |
| 5,823,778 A | 10/1998 | Schmitt et al. |
| 5,829,981 A | 11/1998 | Ziegler |
| 5,851,115 A | 12/1998 | Carlsson et al. |
| 5,857,853 A | 1/1999 | van Nifterick et al. |
| 5,880,962 A | 3/1999 | Andersson et al. |
| 5,938,446 A | 8/1999 | Andersson et al. |
| 5,975,893 A | 11/1999 | Chishti et al. |
| 5,989,029 A | 11/1999 | Osorio et al. |
| 5,993,214 A | 11/1999 | Persson et al. |
| 6,066,274 A | 5/2000 | Antonsson et al. |
| 6,126,445 A | 10/2000 | Willoughby |
| 6,149,433 A | 11/2000 | Ziegler et al. |
| 6,155,828 A | 12/2000 | Lazzara et al. |
| 6,159,010 A | 12/2000 | Rogers et al. |
| 6,168,435 B1 | 1/2001 | Beaty et al. |
| 6,186,790 B1 | 2/2001 | Karmaker et al. |
| 6,210,162 B1 | 4/2001 | Chishti et al. |
| 6,217,331 B1 | 4/2001 | Rogers et al. |

(Continued)

*Primary Examiner*—Cris Rodriguez
*Assistant Examiner*—Candice C Stokes
(74) *Attorney, Agent, or Firm*—Charles W. Hanor

(57) ABSTRACT

The present invention provides a method of making and aligning digital images from oral tissues, dental implants, healing components, and dental restorations to design and manufacture dental implant retained restorations. Image data about the space available for the planned restoration, orientation of dental implants or abutments and aesthetic contour and occlusion of the prosthesis are all integrated into a virtual three-dimensional model of the prosthesis that can be sent to the clinician or laboratory to validate design intent and to manufacture the prosthesis. The virtual model is used by either a conventional rapid prototyping machine to produce a castable pattern or a number controlled mill to machine the restoration.

14 Claims, 8 Drawing Sheets

U.S. PATENT DOCUMENTS

| | | |
|---|---|---|
| 6,227,851 B1 | 5/2001 | Chishti et al. |
| 6,231,342 B1 | 5/2001 | Osorio et al. |
| 6,261,098 B1 | 7/2001 | Persson et al. |
| 6,276,938 B1 | 8/2001 | Jorneus et al. |
| 6,283,752 B1 | 9/2001 | Kumar |
| 6,287,116 B2 | 9/2001 | Lazzara |
| 6,287,119 B1 | 9/2001 | van Nifterick et al. |
| 6,305,939 B1 | 10/2001 | Dawood |
| 6,343,930 B1 | 2/2002 | Beaty et al. |
| 6,354,836 B1 | 3/2002 | Panera et al. |
| 6,361,318 B1 | 3/2002 | Back et al. |
| 6,394,801 B2 | 5/2002 | Chishti et al. |
| 6,419,489 B1 | 7/2002 | Jorneus et al. |
| 6,419,491 B1 | 7/2002 | Ricci et al. |
| 6,431,866 B2 | 8/2002 | Hurson |
| 6,491,723 B1 | 12/2002 | Beaty |
| 6,524,106 B1 | 2/2003 | Ziegler |
| 6,540,516 B1 | 4/2003 | Ziegler |
| 6,558,162 B1 | 5/2003 | Porter et al. |
| 6,607,386 B1 | 8/2003 | Andersson et al. |
| 6,640,150 B1 | 10/2003 | Persson et al. |
| 6,648,645 B1 | 11/2003 | MacDougald et al. |
| 6,652,765 B1 | 11/2003 | Beaty |
| 6,655,962 B1 | 12/2003 | Kennard |

DESIGN AND MANUFACTURE OF DENTAL IMPLANT RESTORATIONS

CROSS-REFERENCE TO RELATED APPLICATIONS

This application claims priority under 35 U.S.C. § 119(e) to U.S. Provisional Patent Application Ser. No. 60/602,390, filed Aug. 17, 2004.

STATEMENTS REGARDING FEDERALLY SPONSORED RESEARCH OR DEVELOPMENT

None

REFERENCE TO A MICROFICHE APPENDIX

None

BACKGROUND OF THE INVENTION

1. Field of the Invention

The present invention relates to methods and systems used in dental restoration. A dental restorative system replaces teeth and tissues missing in a patient's mouth.

2. Description of the Related Art

One prior art design is a dental abutment device that is a replica of the tooth that is to be replaced. The size and shape of the abutment is determined by a computer algorithm that modifies the tooth model based on measurements taken of the site where the tooth is to be replaced. This prior art design for a dental abutment is covered in U.S. Pat. No. 5,989,029 and U.S. Pat. No. 6,231,342.

U.S. Pat. No. 5,829,981 and U.S. Pat. No. 6,149,433 describe a coping device to use in customized implant restoration. The coping device has a head on one end that fits into a dental fixture such as dentures by way of a plurality of axially extending fingers for a radial friction fit onto an implanted dental implant fixture.

A healing abutment and impression coping is described in U.S. Pat. No. 6,155,828. This device attaches to an implant that is in the jawbone of the patient and extends up through the gingival region to allow healing of the gingiva or gum tissue. During the healing process an aperture will be formed by the abutment of this device so as to enable an impression coping to be attached to the upper end of the device. Each aperture can vary in size according to the size of the impression coping, such as a molar, premolar, or incisor.

U.S. Pat. No. 6,524,106 and U.S. Pat. No. 6,540,516 describe devices with platforms for holding and selecting impression copings during various dental procedures. The invention reduces the trial and error of the dental professional in deciding what size impression is needed. This device provides platforms that hold a selection of impression copings that work with available dental fixtures.

U.S. Pat. No. 6,558,162 is a device that provides healing abutments for use during the second stage of dental restoration. The healing abutments have information markers on them that enable the abutments to be left in the patient's mouth until the permanent components are ready to be installed. The information markers allow the dentist to determine the size of both the healing abutment and the implant below the healing abutment, without the removal of the abutment.

U.S. Pat. No. 6,491,723 and U.S. Pat. No. 6,652,765 describe a device that is to be implanted into the jawbone for the connection of an abutment with the jawbone. The device is to have a uniform roughness over the area of the implant that is to bond with the bone. The device will be implanted into the jawbone of a patient and then on top of this device the dentist can attach coping devices for abutments or dentures.

The invention in U.S. Pat. No. 6,210,162 is a technique to reduce the time and cost associated with producing molds for orthodontic appliances. The technique used is a 3D volumetric image of the physical model of the patient's mouth. Then computer-implemented techniques are used to design and simulate orthodontic treatment for the patient.

U.S. Pat. No. 6,217,331 is a device for a dental implant that is to be implanted in a living jawbone. The device is implanted in the jawbone and extends through the gingiva or gum tissue of the patient to connect with an artificial tooth to replace a missing tooth in that location. The gingival section is connected with the anchoring portion of the device, therefore, no seam is present for bacteria to collect in and cause an infection.

U.S. Pat. No. 6,287,116 describes a way to increase the stability of a dental implant in the jawbone of a patient. Stability is increased by improving the tension on the screws used to assemble the dental implants. The screws used in this invention can support a greater amount of tension when they have been coated with gold, and particularly the screws made with titanium and then coated with a biocompatible metal such as platinum, nickel, or copper.

U.S. Pat. Nos. 5,975,893, 6,227,851 and 6,394,801 describe a reconfigurable dental model of a patient's teeth. Each individual member of the manipulable model can move and rotate along three different axial directions. The movement of each member represents a tooth of the patient, and allows a dentist to make orthodontic adjustments to a patient from start to finish with the same 3D model.

One possible example of prior art is where a patient has a denture with a metal clip member attached to the underside of the denture. The patient also has a metal bar that is attached to abutments extending from dental implants in the patient's jawbone. The metal clip attached to the denture can then snap onto the bar in the patient's mouth to hold the denture in place. In this configuration, the denture is removable by simply unsnapping the denture from the bar that is permanently attached to the patient's jawbone.

Another possible example of prior art is when a bridge of two or more teeth is supported by multiple implants. In this procedure the dental implants are implanted into the jawbone of the patient and then the bridge is secured to the abutments extending from the dental implants.

There is also another possible example of prior art which is to permanently secure a denture in the patient's mouth. In this other option the denture can be attached to the abutments on the dental implants by fixation screws.

BRIEF SUMMARY OF THE INVENTION

Patients who wear dentures in one or both dental arches (the upper and lower jawbones) frequently prefer to have dental implants embedded within the jawbone to provide additional support and comfort for their artificial teeth. Patients that have dentures usually experience loss of bone in their jawbone and the gum retracts with the bone. As the bone and gum pull away from the denture there becomes a separation of the gum from the denture and the denture no longer stays in place. With dental implants embedded into the jawbone there is not any loss of bone and there remains a tight fit between the denture and the gum. The process of planning and placing dental implants is well established in the art and generally done in multiple stages.

Every dental implant comprises a metal anchor that is implanted into the jawbone and an abutment or post that extends above the gum line. An artificial tooth or set of teeth are attached to the abutment portion of the dental implant for function and appearance. First the metal anchors of the dental implants are placed in the jawbone and allowed to heal. After healing, an opening is made in the soft tissue or gingival (the gum tissue of the jaw) and a healing abutment is attached to the implant. A healing abutment is a device with a first means that is attached to the metal anchor, and a second means that extends above the soft gum tissue of the patient thereby allowing the gums to heal around the shape of the healing abutment. The use of the healing abutment is to allow the dentist to be able to locate the position of the metal anchor while the gums are healing.

The patient's existing denture is usually "modified" after the healing abutments are connected to the dental implants. Space is created on the bottom of the denture where the denture comes in contact with the gums and then a standard impression material is added to the denture to record the new shape of the gum tissue and healing abutments. After the soft tissue heals, the healing abutments are removed and impression copings are attached to the metal anchors where the healing abutments were. An impression is made of the location of the dental implants and soft tissue by making an impression of the impression copings and the soft gum tissue. The use of the impression copings is extended from the metal anchors above the gum line of the patient so that when the impression is taken, the location of the implants will be known. This is a complex task and after the impression is made and the dental model created, an additional appointment is needed to record the relationship of the implants and tissue to the opposing teeth or denture.

After the molds are taken of the patient's denture, soft tissue, and healing abutments, those molds are scanned into a computer software program. Once all of the scans are inputted they are combined to create a three dimensional virtual model of the patient's soft tissue, dental implants, and any remaining teeth. This virtual model can then be used with different software operations to cut and join restorative components and to design the form of the planned restoration. This planned restoration will incorporate the existing structures of the patient's mouth, such as the implant anchors, the gums, and existing teeth, with a new substructure for the restoration and new artificial teeth. Then the design can be outputted to a conventional rapid prototyping machine or to a number controlled mill to machine the substructure of the restoration.

Once the substructure is made, artificial teeth will be set into the substructure according to the virtual model of the planned restoration. As a final step, minor alterations to the substructure may be made, by way of electric discharge machining, to create ideal fit between the restoration substructure and the dental implant anchors.

DETAILED DESCRIPTION OF THE INVENTION

Figure 1:
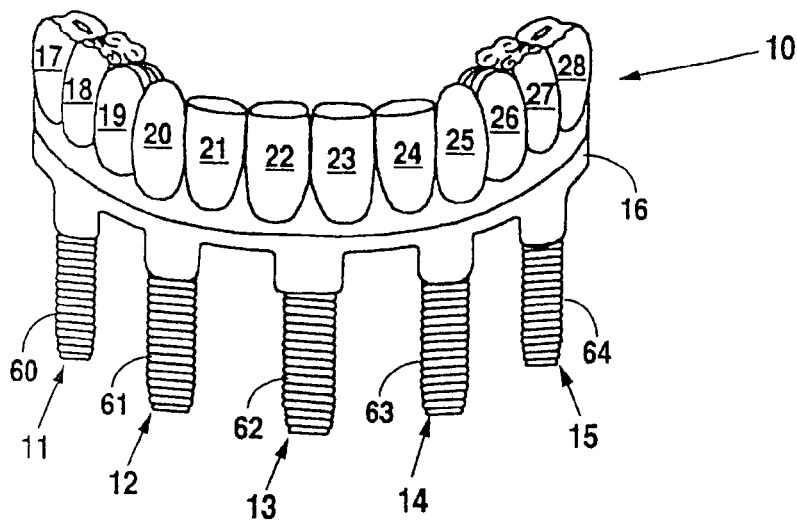
FIG. 1 shows a dental implant fixture with dental implants, a cast substructure, and denture in accordance with this invention.

The present invention relates to a method and system used in dental restoration. A dental restorative system replaces teeth and tissues missing in a patient's mouth. As seen in FIG. 1, dental restorative system 10 comprises dental implant fixtures 11, 12, 13, 14 and 15, dental cast substructure or casting 16, and artificial teeth 17, 18, 19, 20, 21, 22, 23, 24, 25, 26, 27 and 28. Dental implant fixtures 11, 12, 13, 14 and 15 have a first means, metal anchors 60, 61, 62, 63, and 64 (to function as an artificial root), and a second means, abutments or post (not shown) that attaches to an artificial tooth or set of teeth. Metal anchors 60, 61, 62, 63, and 64 can either be metal sleeves inserted into a hole already made in the patient's jawbone or metal screws implanted into the jawbone. After metal anchors 60, 61, 62, 63, and 64 have been implanted, the jawbone is allowed to heal around metal anchors 60, 61, 62, 63, and 64. The abutments or posts of dental implant fixtures 11, 12, 13, 14, and 15 are usually metal attachments that are the size of metal anchors 60, 61, 62, 63, and 64 on one end and taper to the center of the abutment or post at the other end. The top of most abutments or post have an opening that can allow a screw to be inserted into it to attach either an individual artificial tooth, a bridge of teeth, or a complete denture set. The techniques for installing metal anchors 60, 61, 62, 63, and 64 of dental implant fixtures 11, 12, 13, 14 and 15 in the jawbone of a patient are well known. The abutments or posts of dental implant fixtures 11, 12, 13, 14 and 15 will attach to dental cast substructure or casting 16 to anchor the other components of dental restorative system in the proper position and alignment in the mouth. Artificial teeth 17, 18, 19, 20, 21, 22, 23, 24, 25, 26, 27 and 28 provide the function and aesthetic appearance of natural teeth and are supported by dental cast substructure or casting 16 in dental restorative system 10.

Frequently patients already have dentures that restore the proper position of missing teeth. Over time, these dentures loosen and lose their retention to the gums because of the deterioration and loss of the jawbone in the patient's mouth. Dental adhesives are often used to try and maintain the bond between the dentures and the gum tissue of the patient's mouth. These dentures can be used as a guide to record and transfer information about dental implant fixtures 11, 12, 13, 14, and 15 such as the space and shape required for substructure 16 that supports artificial teeth 17, 18, 19, 20, 21, 22, 23, 24, 25, 26, 27 and 28.

Figure 2:
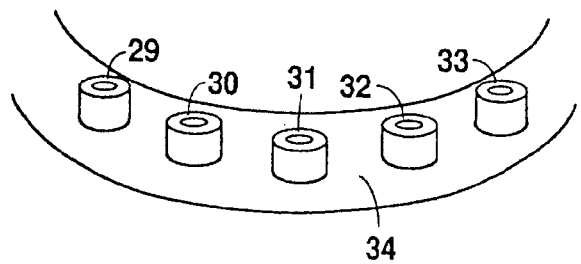
FIG. 2 shows healing abutments above the gingival region (gum line) of a patient.

Referring to FIG. 2, healing abutments 29, 30, 31, 32 and 33 are shown extending through the soft tissue 34 of the gum. After the jawbone of the patient has healed around metal anchors 60, 61, 62, 63, and 64 (shown in FIG. 1) of dental implant fixtures 11, 12, 13, 14, and 15 (shown in FIG. 1) an opening is made in soft tissue 34 and healing abutments 29, 30, 31, 32, and 33 are attached to the top of metal anchors 60, 61, 62, 63, and 64 (shown in FIG. 1). Healing abutments 29, 30, 31, 32, and 33 are used to show the location of dental implant fixtures 11, 12, 13, 14, and 15 (shown in FIG. 1) while soft tissue 34 is healing. The total healing process of the jawbone and soft tissue 34 usually takes place over a few months. The installation of healing abutments is well known and is regularly practiced.

Figure 3:
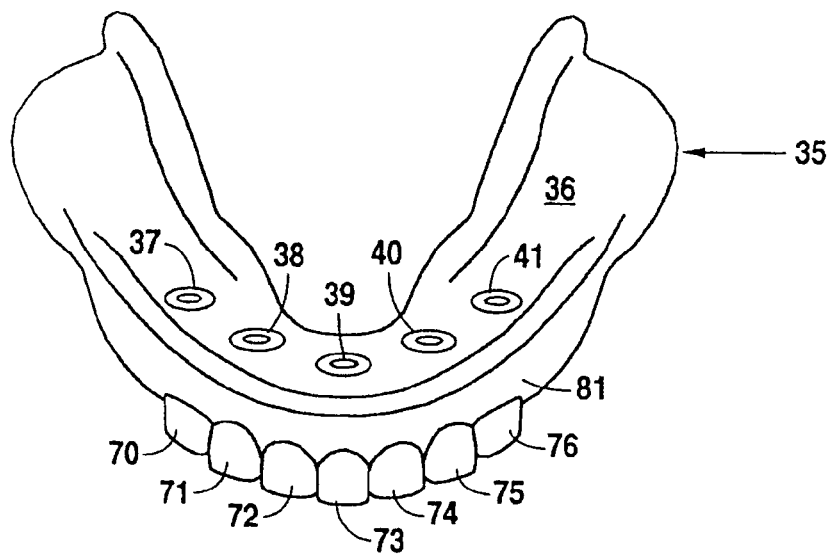
FIG. 3 shows the impression made by the healing abutment in the patient's denture.

The apparatus and method of the invention is more specifically described as follows. Referring to FIGS. 2 and 3, an impression is made of the healing abutments 29, 30, 31, 32 and 33 and soft tissue 34 of the mouth using the patient's denture 35 as a tray. This requires that the healing abutments 29, 30, 31, 32 and 33 protrude only slightly above the gum line so that soft tissue 34 does not grow over them during the healing process. The impression can be done shortly after fixtures 11, 12, 13, 14 and 15 (shown in FIG. 1) are installed or can be done several months after fixtures 11, 12, 13, 14 and 15 (shown in FIG. 1) are installed. Prior procedures were designed to allow the bone to grow into or around the fixtures or implants over several months, but current implants can be screwed into the bone to provide an immediate support that gets stronger over time.

Inside surface 36 of denture 35 has originally rested flush with soft tissue 34; but now that healing abutments 29, 30, 31, 32, and 33 extend above soft tissue 34, denture 35 cannot rest completely on soft tissue 34. In order to make room for the healing abutments 29, 30, 31, 32 and 33, portions 37, 38, 39, 40, and 41 of inside surface 36 of denture 35 are removed, such as by grinding. With portions 37, 38, 39, 40, and 41 removed from denture 35, it is possible for denture 35 to fit over healing abutments 29, 30, 31, 32 and 33 and rest flush with soft tissue 34.

The next step is for a standard impression material to be placed in the patient's existing denture 35. Denture 35 is then put in the mouth with the impression material to form an impression and record the position, orientation and shape of soft tissue 34 and healing abutments 29, 30, 31, 32 and 33. It is also important to determine that denture 35 is in a proper orientation relative to the opposing teeth and supporting soft tissues. This is done by visual observation to make sure that the dentures are in substantially the same position as before. An adhesive can be put into the denture to retain the impression material. After the impression material has set, denture 35 and accompanying set impression material is removed from the mouth. The impression material constitutes a thin layer at the interface between the inside surface of the denture and the gums.

After the impression and denture 35 have been removed from the patient's mouth plaster or casting material is poured into the impression. The cast of the impression can be completed while the patient is in the clinic so that it is not necessary for the patient to leave denture 35 and go home without it.

Figure 4:
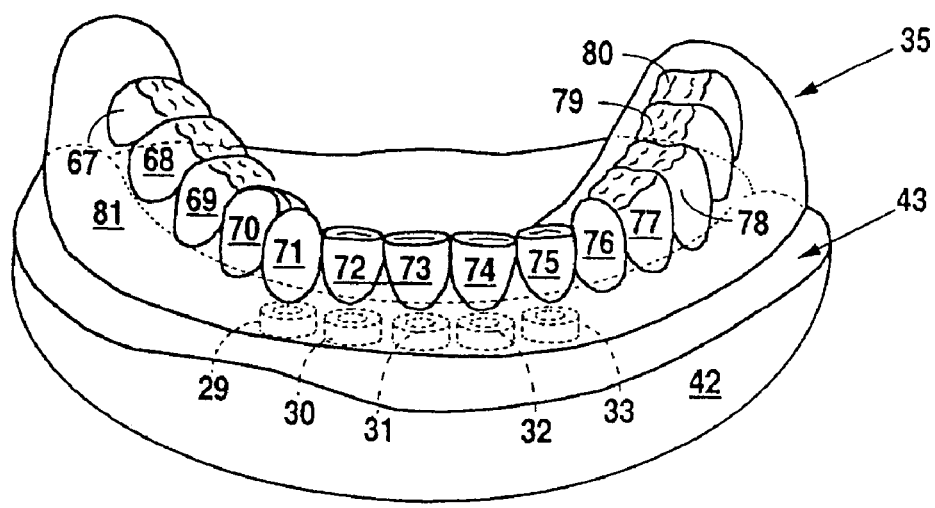
FIG. 4 shows a replica cast of the patient's arch with the denture on top of the cast.

As seen in FIG. 4, dental stone or a similar casting material is used to make the cast from the impression taken with denture 35. The resulting cast is tissue and abutment cast 42 of the patient's arch, and it is a model of soft tissue 34 and healing abutments 29, 30, 31, 32 and 33 and their relationship with denture 35. The casting of tissue and abutment cast 42 is done using standard casting techniques. Although this explanation is made for only one arch, it is understood that two dentures, upper and lower, might be involved. As shown in FIG. 4, the denture 35 is shown placed upon tissue and abutment cast 42 of the patient's dental arch to mimic how it would fit in the patient's mouth with the healing abutments extending from soft tissue 34. Denture 35, placed upon tissue and abutment cast 42, is made up of artificial teeth 67, 68, 69, 70, 71, 72, 73, 74, 75, 76, 77, 78, 79, 80 and artificial teeth support 81.

Figure 5:
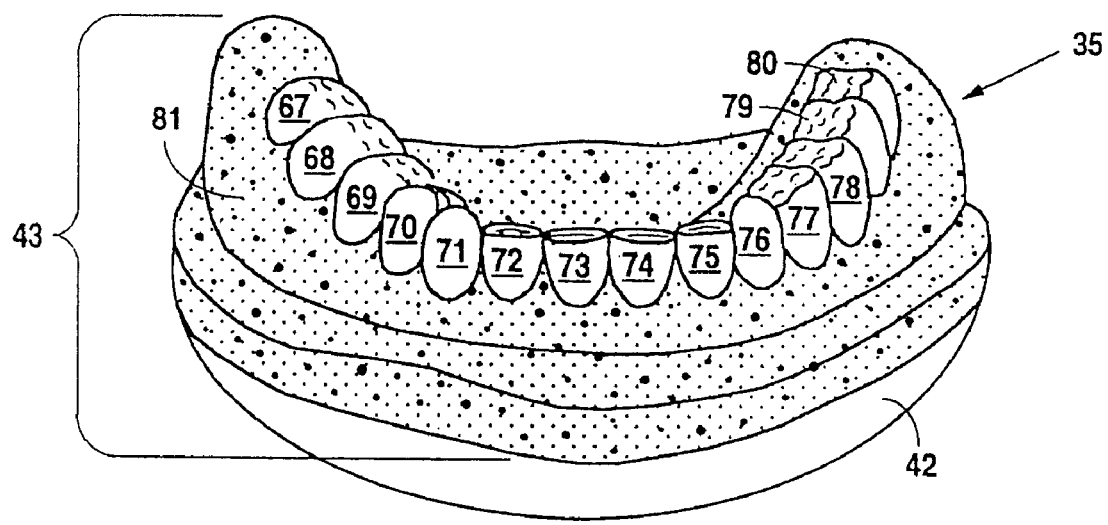
FIG. 5 shows a replica cast and denture with a thin plastic template over both.

Referring to FIG. 5, before the denture 35 is removed from tissue and abutment cast 42, a vacuum or compression molded template 43 is created over the top of the denture 35 using standard vacuum forming techniques. A thin clear plastic sheet is placed upon the denture 35 and tissue and abutment cast 42 and then closely formed in contact with them. This thin template 43 will record the external form of artificial teeth 67, 68, 69, 70, 71, 72, 73, 74, 75, 76, 77, 78, 79, 80 and artificial teeth support 81 that make denture 35, in relation to the tissue and abutment cast 42. Denture 35 can then be removed and returned to the patient.

This leaves the dentist with tissue and abutment cast 42 and thin template 43. These can then be scanned using a digital scanner to form a three dimensional representation of the patient's mouth and denture (described below). The formation of the thin template 43 would be unnecessary if the dentist has a digital scanner available in house and can make the scan of denture 35 on the spot. The thin template 43 allows the scan to be done at a later time without the presence of denture 35.

Figure 13:
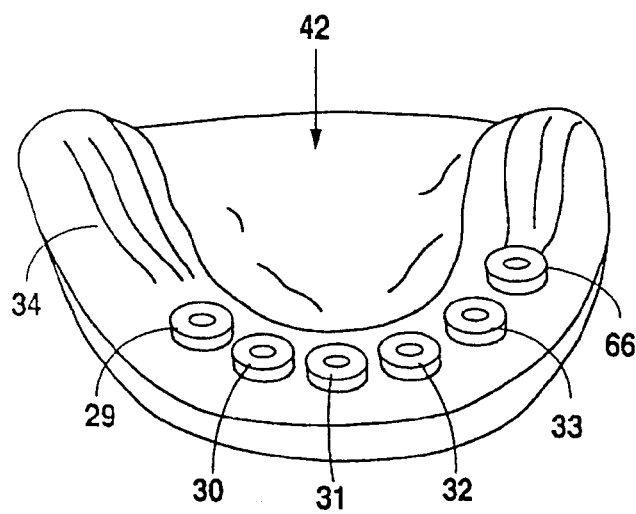
FIG. 13 shows a soft tissue and abutments cast.

Tissue and abutment cast 42 and plastic template 43 are then scanned with light, laser, or contact digitizing to create a digital model of the surface of the denture 35 as well as healing abutments 29, 30, 31, 32 and 33 and soft tissue 34 (seen in FIG. 13). Commercial scanners are available to scan tissue and abutment cast 42 and plastic template 43 or denture 35.

Figure 6:
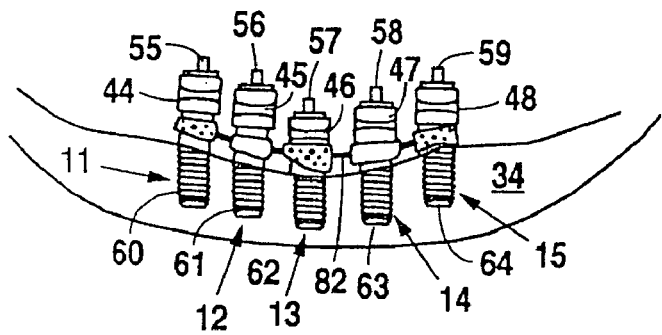
FIG. 6 shows impression copings in the location that the healing abutment were.

Referring to FIG. 6, in a preferred method of the invention the exact positions of metal anchors 60, 61, 62, 63, and 64 of dental implant fixtures 11, 12, 13, 14, and 15 are recorded from the mouth using impression copings 44, 45, 46, 47 and 48 to "pick-up" and create a physical model of dental implant fixtures 11, 12, 13, 14 and 15 with orientation relative to each other. This requires that healing abutments 29, 30, 31, 32, and 33 be removed from dental fixtures 11, 12, 13, 14, and 15. Impression copings 44, 45, 46, 47, and 48 are sleeves that are temporarily attached to the top of metal anchors 60, 61, 62, 63, and 64 of dental implant fixtures 11, 12, 13, 14, and 15. Screws 55, 56, 57, 58, and 59 extend through openings in impression copings 44, 45, 46, 47, and 48 into the screw openings in dental fixtures 11, 12, 13, 14, and 15 to secure impression copings 44, 45, 46, 47, and 48 on to fixtures 11, 12, 13, 14 and 15 in place of healing abutments 29, 30, 31, 32 and 33. Impression copings 44, 45, 46, 47, and 48 are then connected together with a settable resin material 82 to capture their orientation to each other. After resin material 82 is set, screws 55, 56, 57, 58, and 59 holding impression copings 44, 45, 46, 47 and 48 can then be unscrewed from fixtures 11, 12, 13, 14 and 15. Any suitable type of setting material or impression material could be used to obtain the orientation of impression copings 44, 45, 46, 47 and 48 which determines the location of fixtures 11, 12, 13, 14 and 15. Impression copings 44, 45, 46, 47, and 48 are still maintained in the same orientation by setting material 82. After impression copings 44, 45, 46, 47, and 48 have been removed from metal anchors 60, 61, 62, 63, and 64 the abutments or posts of dental implant fixtures 11, 12, 13, 14, and 15 can be attached to metal anchors 60, 61, 62, 63, and 64. With the abutments or posts attached, dental implant fixtures 11, 12, 13, 14, and 15 are ready to be attached to the rest of dental restorative system 10.

Figure 7:
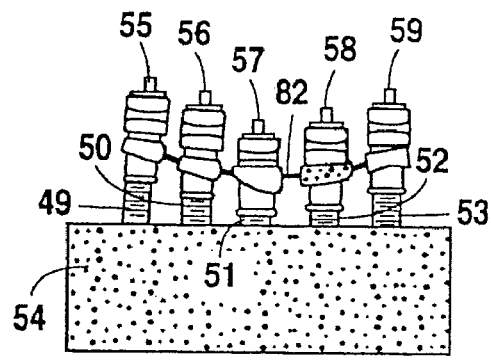
FIG. 7 shows the laboratory analogs secured on the end of the copings closest to the gums.

In FIG. 7, after setting material 82 has set so that the orientation of impression copings 44, 45, 46, 47, and 48 is fixed, laboratory replicas 49, 50, 51, 52 and 53 are then secured on the end of impression copings 44, 45, 46, 47 and 48 that was closest to the gums. This is a common process in the art and it is used to validate the position of the laboratory replicas 49, 50, 51, 52 and 53. Laboratory replicas 49, 50, 51, 52 and 53 are then embedded in dental stone 54 or a similar material that rigidly maintains their spatial relationship and orientation to each other. Dental stone 54 is also placed in a fixturing device which fixes its position to maintain its orientation to a scanner.

Figure 8:
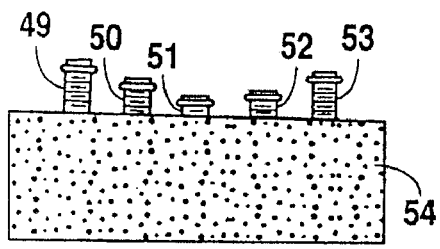
FIG. 8 shows the laboratory analogs in dental stone with the exact orientation to be scanned digitally.
Figure 9:
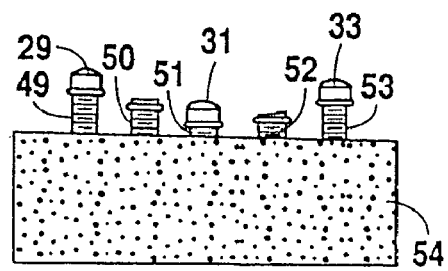
FIG. 9 shows the laboratory analogs with three healing abutments attached for a digital scan.

Referring to FIG. 8, the exposed coronal surfaces of the laboratory replicas 49, 50, 51, 52 and 53 extend from the dental stone 54 to be scanned (as described below). In FIG. 9, healing abutments 29, 31, and 33 are attached to laboratory replicas 49, 51, and 53. Ideally these are three of the actual healing abutments the patient was wearing when the impression was made with the denture 35. An alternative technique would use similar abutments that the manufacturer created to tight tolerances. Generally use of three abutments is needed to provide an accurate scan (as described below).

Since over 40 implant companies manufacture hundreds of implant components, the use of virtual parts that are designed to fit each company's implant saves money, time and improves the quality of the planned device. Using solid modeling and Boolean operations it is possible to create custom 3D design models for a specific patient. This model can then be sent to the dental laboratory or dentist via the Internet to validate design intent prior to the manufacture of the casting or machined metal substructure (as described below). Any errors that occur due to casting or machining can be corrected with electric discharge machining as described in U.S. Pat. No. 5,690,843.

Figure 10:
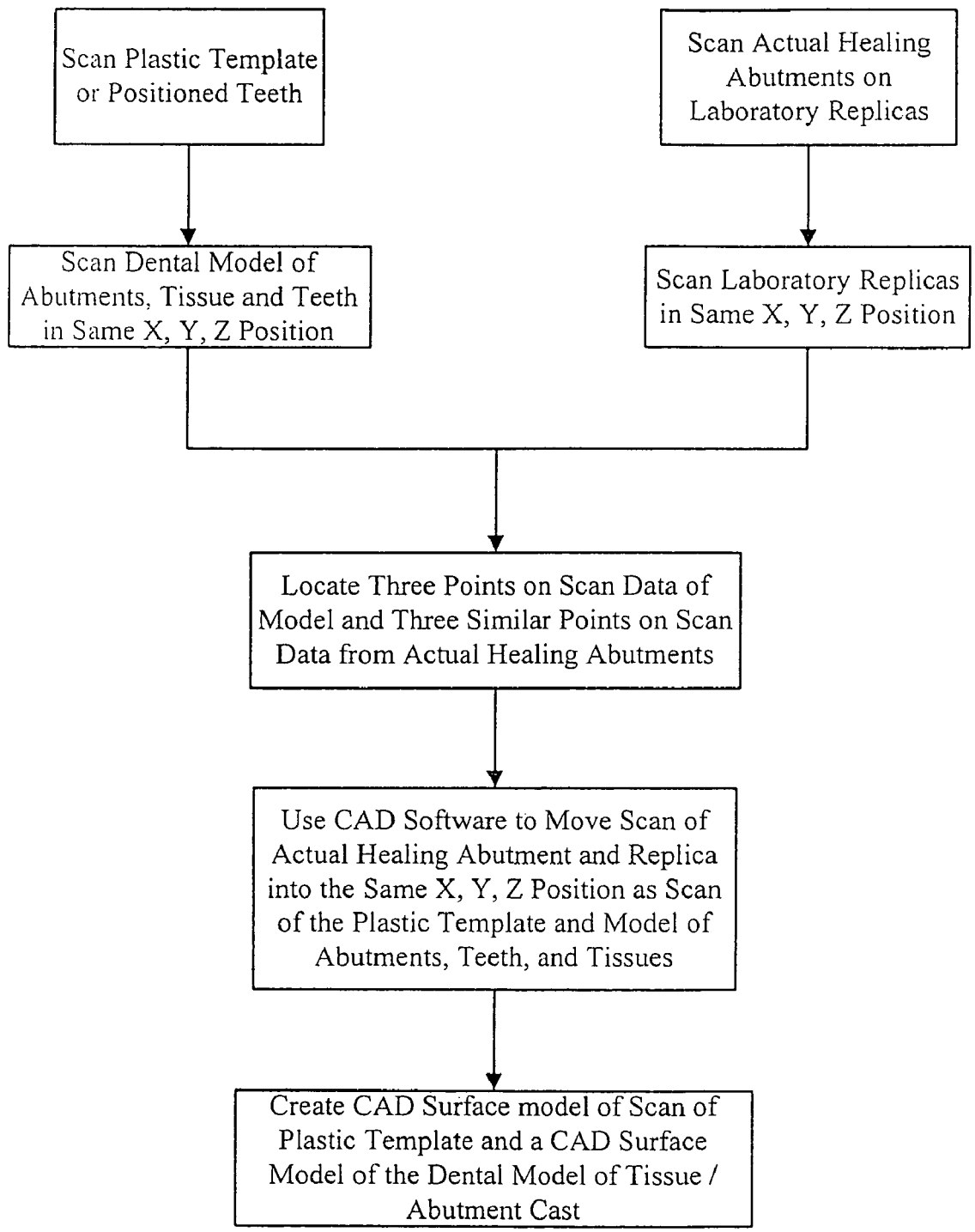
FIG. 10 shows a flow chart listing the steps of this invention to turn the molds into virtual models in computer software.
Figure 11:
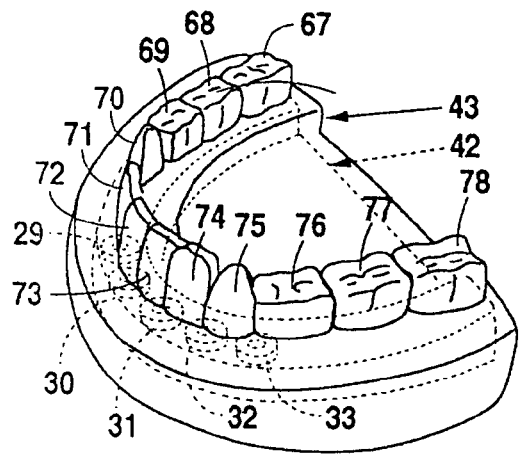
FIG. 11 shows a tissue and abutment cast with a plastic template on it.
Figure 12:
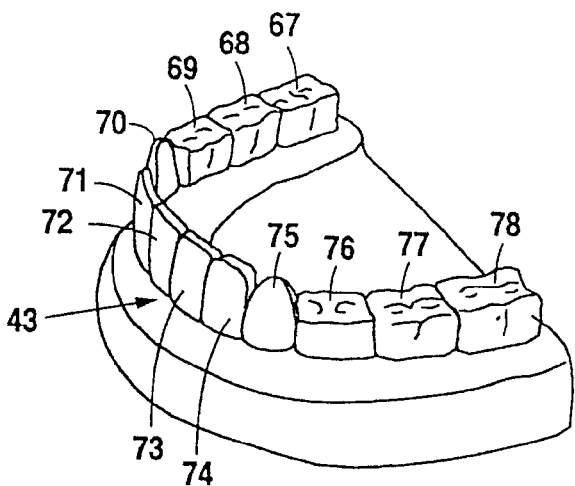
FIG. 12 shows a plastic template.
Figure 14:
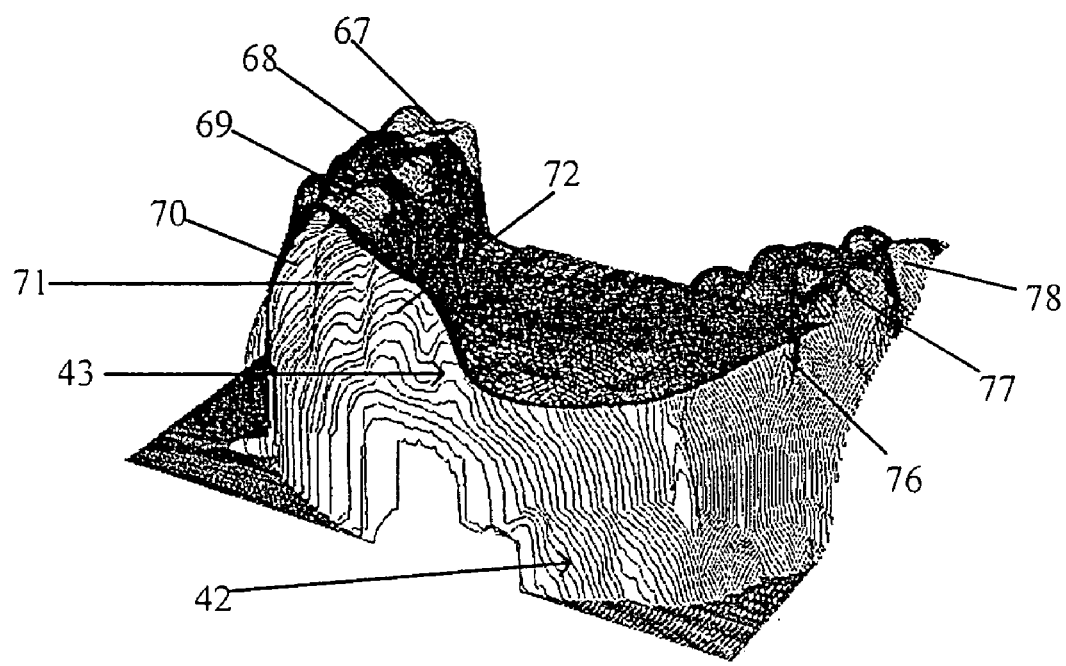
FIG. 14 shows a scan of the plastic model.
Figure 15:
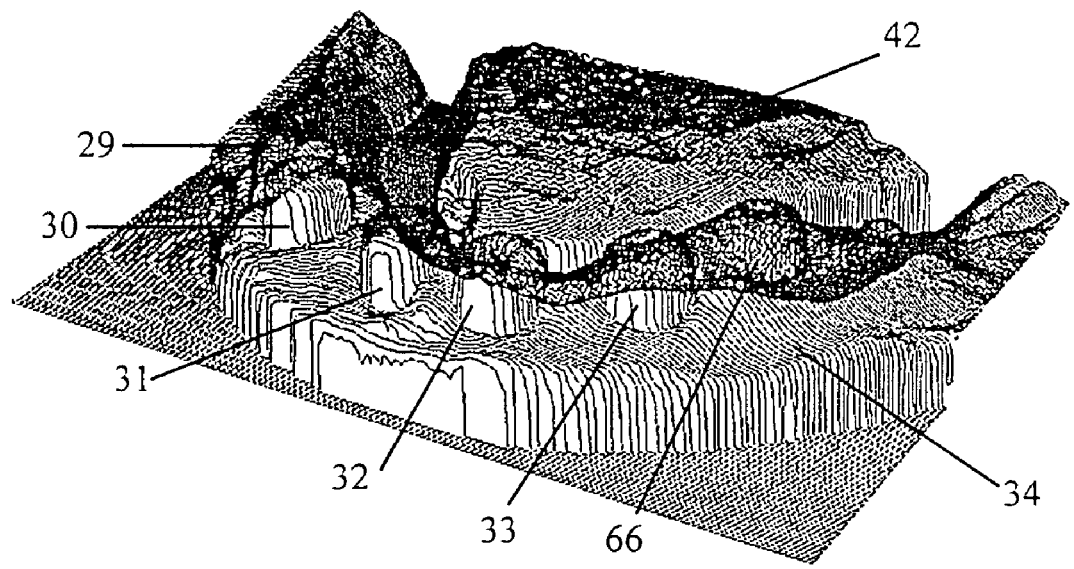
FIG. 15 shows a scan of the soft tissue and abutments cast.

Referring to FIG. 10, there is a flow chart describing the typical steps used to practice the invention. The steps include is that you scanning plastic template 43 made from the patient's denture or other positioned teeth set by a dental technician on a base made to fit over the model of tissue 34 and healing abutments 29, 30, 31, 32, and 33 (shown in FIG. 11). Seen in FIG. 11, plastic template 43 is mounted on top of tissue and abutment cast 42 as they would be scanned. After scanning plastic template 43 (shown in FIG. 12), it can be removed from tissue and abutment cast 42. The steps also include scanning a dental model of healing abutments 29, 30, 31, 32, and 33, tissue 34 (tissue and abutment cast 42 shown in FIG. 13), and remaining teeth in the same XYZ position. In FIG. 13 tissue and abutment cast 42 has an additional healing abutment 66 along with soft tissue 34, and healing abutments 29, 30, 31, 32, and 33. With both the scan of plastic template 43 and the scan of tissue and abutment cast 42 having the same XYZ orientation, the orientation of the external surface of plastic template 43 can be properly oriented with soft tissue 34 and healing abutments 29, 30, 31, 32 and 33 (tissue and abutment cast 42). This provides a three dimensional template of the planned position of the artificial teeth. The scanning may be done on any 3D or three axis scanner such as a conventional contact digitizer scanner having a small size probe, such as a MaxNC scanner (4122-A WEST VENUS WAY Phone: 480-9409414 Chandler, Ariz. 85226 Fax: 480-9402384 (888) 327-9371). This inexpensive contact digitizer creates a data file of the contact points in text code. A laser or light scanner could also be used. The data file can then be converted to a DXF format file with a software conversion program such as provided by MaxNC. The scan of the clear plastic template 43 is shown in FIG. 14 and the scan of tissue and abutment cast 42 (from FIG. 13) is shown in FIG. 15.

Figure 16:
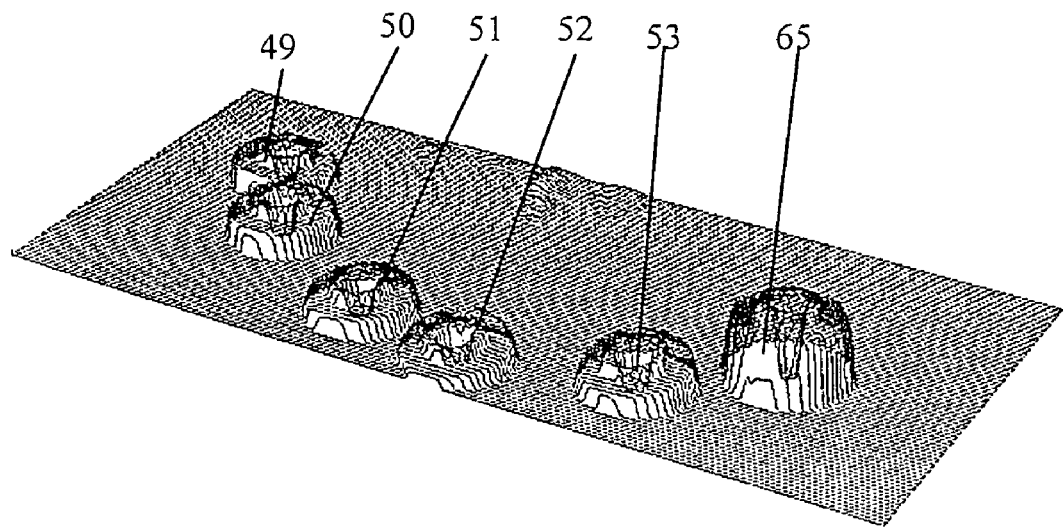
FIG. 16 shows a scan of the replicas.
Figure 17:
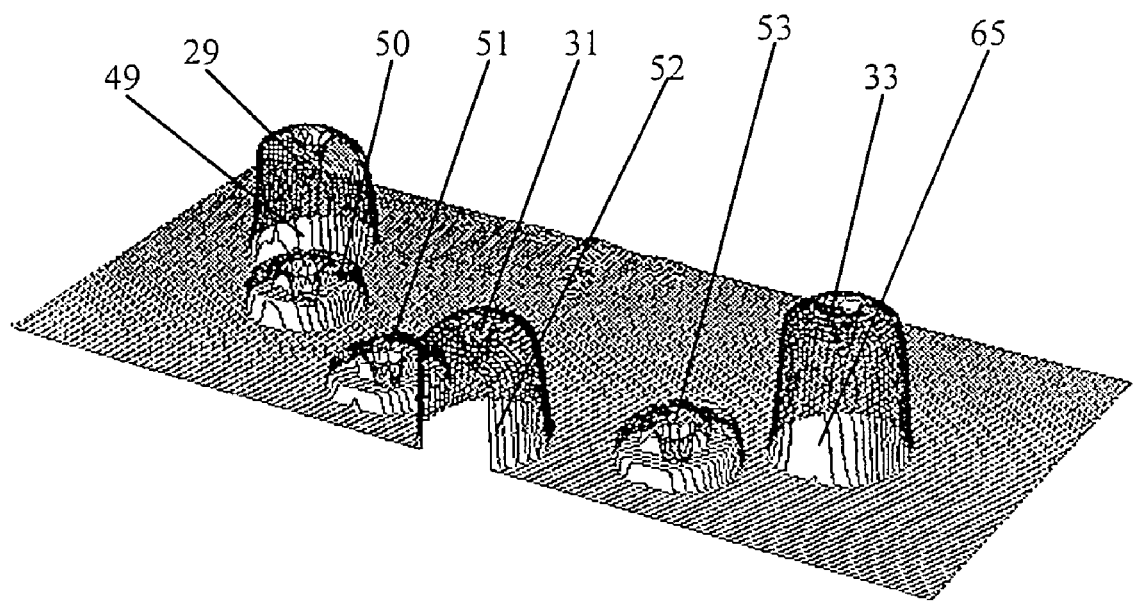
FIG. 17 shows a scan of the replicas and healing abutments.

Next laboratory replicas 49, 50, 51, 52 and 53, from FIG. 8, are scanned and recorded as a text file with MaxNC software. FIG. 16 shows an actual scan of a set of laboratory replicas such as laboratory replicas 49, 50, 51, 52, and 53 with an additional laboratory replica 65. Then, healing abutments 29, 31 and 33 are attached to the laboratory replica with the same position and a second scan is made in the same XYZ orientation as the scan of just laboratory replicas 49, 50, 51, 52, 53 and 65 (shown in FIG. 17).

These four scans are then used to design a solid model of the planned dental restorative system 10. First the scan of model plastic template 43 (shown in FIG. 14) and the scan of tissue and abutment model or cast 42 (shown in FIG. 15) can be joined together to make one new scan of both models since they were scanned in the same XYZ orientation. Next the scan of the actual laboratory replicas 49, 50, 51, 52, 53 and 65 (shown in FIG. 16) and the scan with healing abutments 29, 31 and 33 attached to laboratory replicas 49, 52 and 65 (shown in FIG. 17) can be joined together to make a new scan. The new scan is the combination of both the actual replicas and the actual healing abutments on the replicas since they were scanned with the same XYZ orientation.

Then, using a CAD program, and the data from the two new scans three points on the scan data of the models and three corresponding points on the scan data from actual laboratory replicas and healing abutments are located. CADKEY or similar software may be used to find three corresponding points on each scan data to move the scan of actual laboratory replicas and actual healing abutments into the same XYZ position or orientation as the scan of plastic template 43 and model of abutments 29, 30, 31, 32, and 33, tissue 34, and teeth (tissue and abutment cast 42), shown in FIGS. 14 and 15. The moving of one scan into the XYZ orientation of another can be done using a CADKEY software function called XFORM old-new. Once both scans are in the same XYZ orientation, they are combined together to make a single scan that has most of the necessary components to make dental restorative system 10 (seen in FIG. 1). From this new scan a CAD surface model of the scan of plastic template 43 (shown in FIG. 14) is created, and a CAD surface model of the dental model of tissue and abutment cast 42 (shown in FIG. 15), both with the same XYZ orientation. This is done by importing the DXF format files of each scan into a surfacing software program such as Rhinoceros software sold by Robert McNeel and Associates. Additional software called Plug-ins can be added to Rhinoceros software to provide additional functions. Floating Point Solutions software sold by Goa of India provides point extraction and surfacing plug-ins that extract point data and then create a surface from the points. The surface data can then be output from the Rhinoceros software as an STL format file.

Figure 18:
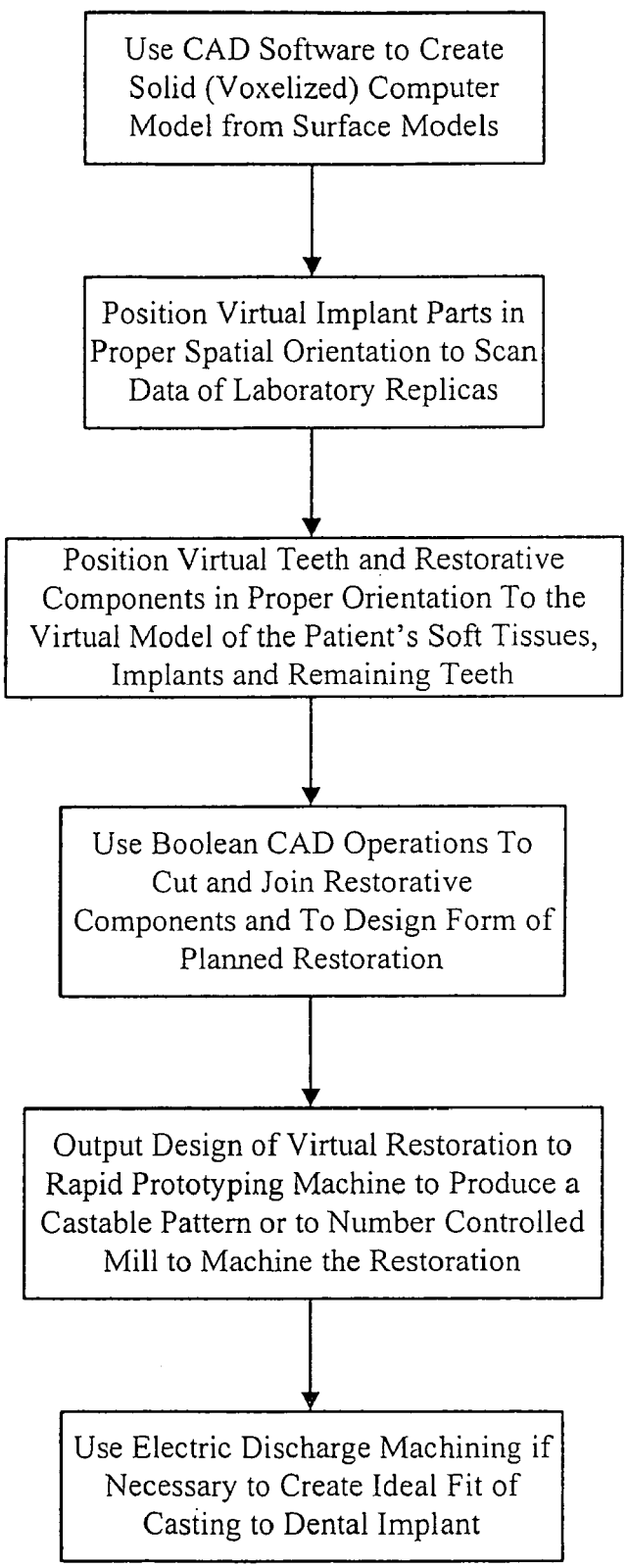
FIG. 18 shows a flow chart of steps to make the restoration of this invention from a three dimensional computer model.

FIG. 18 is a flow chart with the steps necessary for this invention to take the CAD model and create the final planned dental restoration system 10 (shown in FIG. 1). After the surface models are made, CAD software may be used to create a solid (voxelized file format) computer model. The software allows for Boolean operations that are easy for any dentist, dental technician or surgeon to interact with. From this computer model virtual implant parts may be position in the proper spatial orientation to the scan data of laboratory replicas 49, 50, 51, 52, 53, and 65. This allows positioning of the virtual teeth and restorative components in proper spatial orientation to the virtual model of the patient's soft tissue 34, dental implants 11, 12, 13, 14, and 15 and any remaining teeth. One disadvantage of using a voxelized file is that the size of the file becomes very large when smaller and smaller voxels are used to create the model. Image data about the precise location of each replica is determined by scanning the second scan.

The voxelized model is used to create the shape of the planned dental restoration system 10 (shown in FIG. 1). A voxel is short for volume pixel, the smallest distinguishable box-shaped part of a three-dimensional image. Voxelization is the process of adding depth to an image using a set of cross-sectional images known as a volumetric dataset. These cross-sectional images (or slices) are made up of pixels. The space between any two pixels in one slice is referred to as interpixel distance, which represents a real-world distance. And, the distance between any two slices is referred to as interslice distance, which represents a real-world depth. The dataset is processed when slices are stacked in computer memory based on interpixel and interslice distances to accurately reflect the real-world sampled volume.

In the next step, additional slices are created and inserted between the dataset's actual slices so that the entire volume is represented as one solid block of data. Now that the dataset exists as a solid block of data, the pixels in each slice have taken on volume and are now voxels.

For a true 3D image, voxels must undergo opacity transformation. Opacity transformation gives voxels different opacity values. This is important when it is crucial to expose interior details of an image that would otherwise be hidden by darker more opaque outside-layer voxels. Voxel images are primarily used in the field of medicine and are applied to X-Rays, CAT (Computed Axial Tomography) Scans, and MRIs (Magnetic Resonance Imaging) so professionals can obtain accurate 3D models of the human body.

The next step in the FIG. 18 flow chart is to use Boolean operations to cut and join restorative components and to design the form of the planned restoration. This type of software may cover a wide range of functions, including verification, conversion, and repair functions of IGES and VDA-FS models to faceted STL, all the way down to the contour level. With the STL modeling tools, it is possible to manipulate faceted models in a similar way that a CAD system manipulates solids, from offsetting and other advanced tools, up to designing new parts, and cutting/combining them with models retrieved from customer files.

A next step is to output the design of virtual restoration to a conventional rapid prototyping machine to produce a castable pattern or to a number controlled mill to machine the restoration. The combining of the different models in the computer software allows the dentist to produce the complete dental restorative system 10, seen in FIG. 1, in one milling or machining process. The computer software can export the data necessary to make the entire dental restorative system 10 to a single machine that will produce dental substructure casting or cast 16 and the locations of the attachments of dental implant fixtures 11, 12, 13, 14, and 15 on dental substructure casting or cast 16. With the majority of dental restorative system 10 being produced in one step as stated above only the individual artificial teeth need to be positioned on dental substructure casting or cast 16 before dental restorative system 10 is ready to be secured on dental implant fixtures 11, 12, 13, 14 and 15 in the patient's mouth. The ability to produce dental restorative system 10 in one milling or machining process saves both money and time in the production of dental restorative systems. The final step is that an electric discharge machining may be use to create ideal fit of the restoration to the dental implant position as needed.

While the above detailed description describes a preferred embodiment and best mode of the invention, it should be understood and apparent to those skilled in the art that various other embodiments of the invention can be created without departing from the spirit and scope of the invention, which is defined in the claims that follow.

We claim:

1. A method of creating a dental restoration customized to the clinical needs of a patient comprising the steps of:
   preparing a patient's existing dental structures for digital modeling wherein the existing dental structures may comprise implant anchors, soft tissue, jawbone, existing teeth, and an existing denture;
   making a first three-dimensional digital model of the dental restoration wherein the first three-dimensional digital model comprises the implant anchors, soft tissue form, any existing teeth, and the planned position of one or more artificial teeth;
   creating a second three-dimensional digital model of the dental restoration wherein the second three-dimensional digital model comprises a substructure for attaching to the patient's existing dental structures and for retaining the artificial teeth;
   producing the substructure from the second three-dimensional digital model;
   positioning and securing the artificial teeth on the substructure; and
   securing the substructure to the patient's existing dental structures.

2. The method of claim 1 wherein the patient's existing dental structures includes a first set of implant anchors wherein each implant anchor has an end exposed above the patient's gingival tissue and an end implanted in the jawbone of the patient and wherein the step of preparing the patient's existing dental structures for digital modeling comprises the steps of:
   cutting away gingival tissue from around the exposed ends of the first set of implant anchors to allow for the placement of healing abutments on the exposed ends of the first set of implant anchors; and
   placing a healing abutment on the exposed end of each of the first set of implant anchors.

3. The method of claim 1 wherein the step of preparing the patient's existing dental structures for digital modeling comprises the steps of:
   installing a first set of implant anchors within the patient's jawbone, wherein the implant anchors have an end exposed above the patient's gingival tissue and an end implanted in the jawbone;
   cutting away gingival tissue from around the exposed ends of the first set of implant anchors to allow for the placement of healing abutments on the exposed ends of the first set of implant anchors;

placing a healing abutment on the exposed end of each of the first set of implant anchors;

boring holes in the bottom of the patient's existing denture, wherein the holes are of a sufficient dimension and are place appropriately to allow the dentures to fit over the healing abutments; and waiting for a time period sufficient for the patient's gingival tissue to heal before proceeding with additional dental restoration steps.

4. The method of claim 1 wherein the patient's existing dental structures includes a first set of implant anchors wherein each implant anchor has an end exposed above the patient's gingival tissue and an end implanted in the jawbone of the patient and wherein the step of making a first three-dimensional digital model comprises the steps of:

making a first digital model of the patient's jaw with a healing abutment attached to the exposed end of each of the first set of anchors;

making a second digital model of the patient's existing dental structures;

making a third digital model of the precise orientation of the implant anchors within the patient's jawbone;

making a combined digital model by aligning and combining the first, second, and third digital models; and creating a final solid digital model of the entire dental restoration.

5. The method of claim 4 wherein the step of making a first digital model comprises the steps of:

making a first impression of the patient's jaw with a healing abutment attached to the exposed end of each of the first set of anchors;

making a first cast of the first impression; and digital scanning the first cast.

6. The method of claim 4 wherein the step of making a second digital model comprises the steps of:

making a first impression of the patient's jaw with a healing abutment attached to the exposed end of each of the first set of anchors;

making a first cast of the first impression;

placing the existing denture on the first cast;

making a thin template of the combine structure of the denture and first cast; and digitally scanning of the combined structure.

7. The method of claim 4 wherein the step of making a third digital model comprises the steps of:

removing the healing abutments from the exposed ends of the first set of anchors;

securing interconnected impression copings on the exposed ends of the first set of anchors to record the spatial relationship of the anchors to one another;

removing the interconnected impression copings from the exposed ends of the first set of anchors;

forming a single structure by attaching to the impression copings a second set of anchors, wherein the second set of anchors are of a similar make and model to the first set of anchors and wherein the second set of anchors have a top end and a bottom end and wherein the top end of each anchor is attached to the impression coping;

setting the bottom ends of the second set of anchors in a dental stone or similar material to create a lab replica of the patient's jawbone with the first set of anchors implanted therein;

removing the interconnected impression copings from the top ends of the second set of anchors; and digitally scanning the lab replica.

8. The method of claim 7 wherein the step of making a combined digital model comprises the steps of:

defining the healing abutments to be included in a subset of healing abutments wherein the subset is of a sufficient number to provide a precise spatial orientation of the first digital model;

attaching the subset of the healing abutments to the top ends of the second set of anchors;

creating a fourth digital model by digitally scanning the lab replica with the attached healing abutments;

identifying within the first digital model a first set of coordinates of each of the healing abutments included in the subset;

identifying within the fourth digital model a second set of coordinates of each of the healing abutments included in the subset;

combining the first digital model and the second digital model into a fifth digital model;

combining the third digital model and the fourth digital model into a sixth digital model; and combining the fifth digital model and the sixth digital model into a combined digital model by aligning the first set of coordinates with the second set of coordinates.

9. The method of claim 4 wherein the step of creating a final solid digital model of the entire dental restoration comprises the steps of:

creating a digital surface model of the combined digital model;

voxelizing the digital surface model to create a first digital solid model of the existing dental structures;

creating digital virtual models of one or more artificial teeth to be used in the production of the patient's customized dental restoration;

creating a second solid digital model of the dental restoration by positioning the digital virtual models of the artificial teeth in proper spatial orientation to the first solid digital model; and creating the final solid digital model of the dental restoration by smoothing and altering the digital representation of the existing denture surface in the second solid digital model.

10. The method of claim 1 wherein the step of creating a second three-dimensional digital model of the dental restoration comprises the steps of digitally removing the artificial teeth, the implant anchors, the soft tissue, and the jawbone from the first three-dimensional model of the dental restoration.

11. The method of claim 1 wherein the step of producing the substructure comprises the step of outputting the second three-dimensional digital model to a machine capable of producing the substructure from materials suitable for use in a patient's mouth.

12. The method of claim 11 wherein the machine is a rapid prototyping machine.

13. The method of claim 11 wherein the machine is a numerically-controlled milling machine.

14. The method of claim 1 further comprising the step of electronically sending the first three-dimensional digital model to the patient's dental professional for verification of the accuracy of the model.

* * * * *